United States Patent
Brown et al.

[11] Patent Number: 5,817,698
[45] Date of Patent: Oct. 6, 1998

[54] SUBSTITUTED CYCLOALKYLAMINE DERIVATIVES AND THEIR USE AS CALCIUM CHANNEL ANTAGONISTS

[75] Inventors: Thomas Henry Brown, Tewin; John David Harling, Harlow; Barry Sidney Orlek, Epping, all of England

[73] Assignee: SmithKline Beecham plc, Brentford, United Kingdom

[21] Appl. No.: 704,585

[22] PCT Filed: Mar. 14, 1995

[86] PCT No.: PCT/EP95/00964

§ 371 Date: Sep. 20, 1996

§ 102(e) Date: Sep. 20, 1996

[87] PCT Pub. No.: WO95/26327

PCT Pub. Date: Oct. 5, 1995

[30] Foreign Application Priority Data

Mar. 26, 1994 [GB] United Kingdom .................. 9406043

[51] Int. Cl.$^6$ ................................................. A61K 31/135
[52] U.S. Cl. .................... 514/646; 514/659; 564/397; 564/443; 564/446; 564/454
[58] Field of Search .................... 564/453, 397, 564/446, 443, 454; 514/646, 659

[56] References Cited

FOREIGN PATENT DOCUMENTS

| | | | |
|---|---|---|---|
| 0 339 600 | 4/1989 | European Pat. Off. | C07C 87/458 |
| WO 95/04027 | 2/1995 | WIPO | C07C 211/42 |
| WO 95/04028 | 2/1995 | WIPO | C07C 211/53 |

OTHER PUBLICATIONS

Belleu, et al., "Conformation of N–(βChloroethyl)–2–phenoxyethylamines in Relation to Adrenergic Blocking Activity", *Journal of Medicinal Chemistry*, 6 pp. 579–583 (1963).

Anchisi, et al., "An Investigation into the Electron–ionization induced Mass Spectrometric Behaviour of some trans- and cis–Substituted Cycloalkylamines of Pharmaceutical Interest", *Rapid Communications in Mass Spectrometry*, 7 pp. 1–5 (1993).

*Primary Examiner*—Brian M. Burn
*Attorney, Agent, or Firm*—Wayne Dustman; Charles M. Kinzig

[57] ABSTRACT

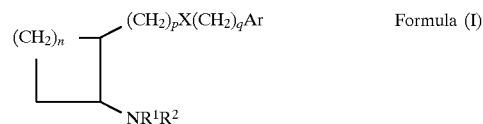

Formula (I)

A method of treatment of a condition or disease related to the accumulation of calcium in the brain cells of a mammal which comprises administering to a subject in need thereof an effective amount of a compound of formula (I), wherein X is O, S, C=O or a bond; p and q are independently 0–4; $R^1$ and $R^2$ are each independently selected from the group consisting of hydrogen, $C_{1-6}$alkyl, $C_{3-6}$cycloalkyl or $C_{3-6}$cycloalkyl$C_{1-4}$alkyl; n is 1, 2, 3 or 4; and Ar is phenyl optionally substituted by 1 to 3 substituents selected from; halo, $C_{1-4}$alkyl, $C_{1-4}$alkoxy, $C_{1-2}$alkylenedioxy, trifluoromethyl, trifluoromethoxy, CN, $NO_2$, amino, mono- or di-alkylamino and Ph(Alk$^1$)$_r$Y(Alk$^2$)$_s$— where Ph is optionally substituted phenyl, Y is a bond, oxygen or a carbonyl group, Alk$^1$ and Alk$^2$ are independently $C_{1-4}$alkyl which may be straight or branched and r and s are independently 0 or 1, provided that the length of (Alk$^1$)$_r$Y(Alk$^2$)$_s$ does not exceed 5 atoms, and pharmaceutically acceptable salts thereof; in the manufacture of a medicament for the treatment of a disorder wherein a calcium channel antagonist is indicated, e.g. ischaemic stroke. Certain novel compounds within formula (I) are also claimed.

13 Claims, No Drawings

SUBSTITUTED CYCLOALKYLAMINE DERIVATIVES AND THEIR USE AS CALCIUM CHANNEL ANTAGONISTS

This application is a 371 of International Application No. PCT/EP95/00964, filed Mar. 14, 1995.

The present invention relates to carbocyclic derivatives, processes for their reparation, pharmaceutical compositions containing them and their use in therapy, in particular as calcium channel antagonists, e.g. for the treatment of ischaemic stroke.

Stroke is reportedly the third most common cause of death in the developed world. Current therapies for ischaemic stroke are limited and have a number of disadvantages, such as the risk of exacerbating haemorrhage. There is therefore a need for new and improved treatments for ischaemic stroke.

DE 3231912 describes aminocyclohexylmethylaniline derivatives; no pharmaceutical activity is ascribed to the compounds. DE 4010325 discloses phenoxycarbocyclic derivatives which are said to have insecticidal activity and intermediates therefor. Teller and Jarboe (J. Med. Chem. (1982) 25 (3) 227) describe cis-and trans-2-(3,4-dimethoxybenzyl)cyclopentylamine, said to be transient hypotensive agents.

EPA 200101 describes therapeutic compositions comprising as active ingredient one of a very broad class of compounds of the formula:

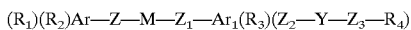

$(R_1)(R_2)Ar—Z—M—Z_1—Ar_1(R_3)(Z_2—Y—Z_3—R_4)$ wherein Ar and $Ar_1$ are independently phenyl, naphthyl, or a nitrogen, oxygen or sulphur ring; $R_1$, $R_2$ and $R_3$ are selected from a wide range of substituents; $R_4$ is also selected from a wide range of acyclic and cyclic substituents, including saturated and unsaturated carbocyclic and heterocyclic rings, which include inter alia cyclopentane and cyclohexane, substituted by $(XR_6)_n$ where X is O, S or $NR_8$ ($R_8$ is H or lower alkyl), $R_6$ is inter alia H or lower alkyl and n is 0 or 1; Z, $Z_1$, $Z_2$ and $Z_3$ are independently a bond or an alkylene chain; Y is inter alia a bond, O, S or CO; and M is inter alia O. The more preferred compounds are said to be those wherein Ar is quinoline and in the substituent $(XR_6)_n$ X is O. The specification contains only a few examples or named compounds wherein $R_4$ is cyclohexyl or cyclopentyl and in each of them the ring is substituted by either a hydroxy or methoxy group. No compounds containing an amino-substituted, saturated, 4-7-membered carbocyclic ring are specifically named or exemplified. The compounds described in EPA 200101 are said to be lipoxygenase inhibitors possessing anti-inflammatory and anti-allergic properties.

We have now found a distinct class of amino-substituted carbocyclic derivatives which represent a novel selection with respect to the compounds described in EPA 200101 and which surprisingly exhibit activity as calcium channel antagonists.

The present invention therefore provides in a first aspect the use of compounds of formula (I):

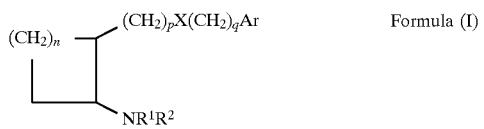

Formula (I)

wherein
X represents O, S, C=O or a bond;
p and q independently represent 0–4;
$R^1$ and $R^2$ each independently represent hydrogen, $C_{1-6}$alkyl, $C_{3-6}$cycloalkyl or $C_{3-6}$cycloalkyl$C_{1-4}$alkyl;
n is 1, 2, 3 or 4; and
Ar represents phenyl optionally substituted by 1 to 3 substituents selected from: halo, $C_{1-4}$alkyl, $C_{1-4}$alkoxy, $C_{1-2}$alkylenedioxy, trifluoromethyl, trifluoromethoxy, CN, $NO_2$, amino, mono- or di- alkylamino and $Ph(Alk^1)_rY(Alk^2)_s$- where Ph is optionally substituted phenyl, Y is a bond, oxygen or a carbonyl group, $Alk^1$ and $Alk^2$ independently represent $C_{1-4}$alkyl which may be straight or branched and r and s are independently 0 or 1, provided that the length of $(Alk^1)_rY(Alk^2)_s$ does not exceed 5 atoms; and pharmaceutically acceptable salts thereof in the manufacture of a medicament for the treatment of a disorder wherein a calcium channel antagonist is indicated.

As indicated above certain compounds of formula (I) are believed to represent a novel selection with respect to EPA 200101. In a further aspect therefore the invention provides compounds of formula (IA):

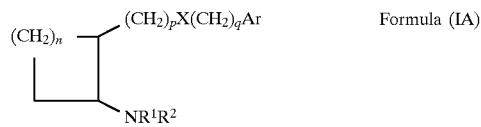

Formula (IA)

wherein
X represents O, S, C=O or a bond;
p and q independently represent 0–4;
$R^1$ and $R^2$ each independently represent hydrogen, $C_{1-6}$alkyl $C_{3-6}$cycloalkyl or $C_{3-6}$cycloalkyl$C_{1-4}$alkyl;
n is 1, 2, 3 or 4; and
Ar represents phenyl optionally substituted by 1 to 3 substituents selected from: halo, $C_{1-4}$alkyl, $C_{1-4}$alkoxy, $C_{1-2}$alkylenedioxy, trifluoromethyl, trifluoromethoxy, CN, $NO_2$, amino, mono- or di- alkylamino and $Ph(Alk^1)_rY(Alk^2)_s$- where Ph is optionally substituted phenyl, Y is a bond, oxygen or a carbonyl group, $Alk^1$ and $Alk^2$ independently represent $C_{1-4}$alkyl which may be straight or branched and r and s are independently 0 or 1, provided that the length of $(Alk^1)_rY(Alk^2)_s$ does not exceed 5 atoms, and salts thereof; provided that: when X is O and p and q are 0, Ar is not phenyl substituted by p-fluorophenoxy, chloro or methyl, and when X is a bond and the sum of p and q is 1, Ar is not unsubstituted phenyl, or phenyl substituted by amino, methoxy, methyl or dimethylamino.

In a yet further aspect the present invention provides the use as a therapeutic agent of a compound of formula (IB) which is defined as for formula (I) above with the proviso that when X is O and p and q are 0, Ar is not phenyl substituted by chloro or methyl, and when X is a bond and the sum of p and q is 1, Ar is not unsubstituted phenyl, or phenyl substituted by amino, methoxy, methyl or dimethylamino.

In the compounds of formulae (I), (IA) and (IB) when Ar represents phenyl this is advantageously substituted by a group $Ph(Alk^1)_rY(Alk^2)_s$. The sum of r and s is preferably zero or 1. $Alk^1$ and $Alk^2$ preferably independently represent $CH_2$ or when branched, $C(H)(CH_3)$ or $C(CH_3)_2$. When Y is oxygen s is preferably zero and r is preferably zero or 1. When Y is a bond the sum of r+s is preferably 1 or 2, most preferably 1. When Y represents C=O, r and s are preferably both zero. It is preferred that only one of $Alk^1$ and $Alk^2$ represents a branched alkyl moiety; for example if $Alk^1$ represents a branched group such as $C(CH_3)_2$ s is advantageously zero and Y represents oxygen or more preferably a bond.

Suitable substituents for the group Ph include halogen, $C_{1-4}$alkoxy, $C_{1-4}$alkyl, trifluoromethyl and trifluoromethoxy.

Particularly preferred substituents of the formula $Ph(Alk^1)_rY(Alk^2)_s$ thus include benzyloxy, benzyl, benzoyl, phenoxy, 1-methyl-1-phenylethyl, 1-(4-fluorophenyl)-1-methylethyl and 4-fluorophenoxy.

In a particular embodiment of the invention each $Alk^1$ and $Alk^2$ independently represents a straight chain $C_{1-4}$alkyl group, provided that the total number of carbon atoms in $Alk^1$ and $Alk^2$ does not exceed 4. In this embodiment $Ph(Alk^1)_rY(Alk^2)_s$ can be represented by a group $Ph(CH_2)_jY^1(CH_2)_k$, wherein Ph is optionally substituted phenyl, $Y^1$ is oxygen, a carbonyl group or a bond and j and k each independently represent 0–4 provided that the sum of j+k is not greater than 4. Preferably j and k independently represent zero or 1, such that the sum of j and k does not exceed 1. Particularly preferred substituents of the formula $Ph(CH_2)_jY^1(CH_2)_k$- thus include benzyloxy, benzyl, benzoyl, phenoxy, and 4-fluorophenoxy.

Ar preferably represents phenyl substituted by benzyl, 1-methyl-1-phenylethyl, 1-(4-fluorophenyl)-1-methylethyl, benzyloxy, benzoyl, phenoxy or 4-fluorophenoxy.

X preferably represents a bond or oxygen atom, in which case the sum of p and q is preferably from 1 to 3. When X is oxygen, p is preferably zero or 1 and q is preferably zero. When X is a bond the sum of p and q is preferably 1. Most preferably X is oxygen, p is 1 and q is zero.

$R^1$ and $R^2$ preferably independently represent hydrogen or $C_{1-6}$alkyl, eg $C_{1-4}$alkyl, preferably methyl. Most preferably one of $R^1$ and $R^2$ represents hydrogen and the other represents hydrogen or methyl. n is suitably 1 to 4, preferably n is 2.

Alkyl groups present in the compounds of formula (I), alone or as part of another group, can be straight or branched. Thus, a $C_{1-6}$alkyl group may be for example methyl, ethyl, n-propyl, n-butyl, n-pentyl, n-hexyl or any branched isomer thereof such as isopropyl or t-butyl.

In a particularly preferred selection of compounds of formula (I), n is 2, X is oxygen, p is zero or 1 (preferably 1) and q is zero, or X is a bond and the sum of p and q is 1, and Ar represents phenyl substituted by a group $Ph(Alk^1)_rY(Alk^2)_s$- where Ph is phenyl optionally substituted by fluoro, Y is a bond, oxygen or a carbonyl group, $Alk^1$ and $Alk^2$ each independently represent $CH_2$ or $C(CH_3)_2$ and r and s each independently represent zero or 1 provided that the sum of r+s is not greater than 1 and further provided that when X is O and p and q are both 0, Ar is not phenyl substituted by p-fluorophenoxy. Most preferred values for X, p, q and Ar are as defined above.

It will be appreciated that for use in medicine a salt of a compound (I) should be pharmaceutically acceptable. Examples of pharmaceutically acceptable salts include inorganic and organic acid addition salts such as hydrochloride, hydrobromide, sulphate, phosphate, acetate, fumarate, maleate, citrate, lactate, tartrate, methanesulphonate or similar pharmaceutically acceptable inorganic or organic acid addition salts. Other non-pharmaceutically acceptable salts eg oxalates, may be used for example in the isolation of final products and are included within the scope of this invention. Also included within the scope of this invention are solvates and hydrates of formula (I).

It will be appreciated that the compounds of formula (I) contain two or more asymmetric centres. Such compounds will exist as optical isomers (enantiomers). Both the pure enantiomers, racemic mixtures (50% of each enantiomer) and unequal mixtures of the two are included within the scope of the invention. Further, all diastereomeric forms possible (pure enantiomers and mixtures thereof) are within the scope of the invention. In particular it will be appreciated that the substituents on the carbocyclic nucleus may both lie on the same side with respect to the plane of the ring (cis-configuration) or on opposite sides (trans-configuration). Both forms and all mixtures thereof are included within the scope of this invention.

In accordance with convention the (+) and (−) designations used herein indicate the direction of rotation of plane-polarised light by the compounds. The prefix (+) indicates that the isomer is dextrorotatory (which can also be designated d) and the prefix (−) indicates the levorotatory isomer (which can also be designated l).

Particular compounds of the formula (I) include:

(±) cis-1-methylamino-2-(4-benzyloxyphenoxy) cyclopentane;

(±) trans-1-methylamino-2-(4-benzyloxyphenoxy) cyclopentane;

(±) cis-1-methylamino-2-(4-benzyloxybenzyl) cyclopentane;

(±) cis-1-amino-2-(4-benzyloxybenzyl)cyclopentane;

(±) cis-1-amino-2-(4-benzoylphenoxymethyl)cyclopentane;

(±) cis-1-amino-2-(4-benzylphenoxymethyl)cyclopentane;

(±) cis-1-methylamino-2-(4-benzylphenoxymethyl) cyclopentane;

(±) cis-1-amino-2-(3,4-dichlorophenoxymethyl) cyclopentane;

(±) cis-1-Amino-2-[4-(4-fluorophenoxy)phenoxymethyl] cyclopentane;

(±) cis-1-Amino-2-[4-(1-methyl-1-phenylethyl) phenoxymethyl]cyclopentane;

(±) cis-1-Methylamino-2-[4-(1-methyl-1-phenylethyl) phenoxymethyl]cyclopentane;

(±) cis-1-Amino-2-[4-(1-(4-fluorophenyl)-1-methylethyl) phenoxymethyl]cyclopentane;

(±) cis-1-Methylamino-2-[4-(1-(4-fluorophenyl)-1-methylethyl)phenoxymethyl]-cyclopentane; and salts thereof.

The compounds of the present invention can be prepared by processes analogous to those known in the art. The present invention therefore provides in a further aspect, a process for the preparation of compounds of formula (I) which comprises:

(a) to prepare a compound of formula (I) wherein X is O and p and q are both 0, reaction of a compound of formula (II):

Formula (II)

wherein n and Ar are as hereinbefore defined with a compound $R^1R^2NH$ wherein $R^1$ and $R^2$ are as hereinbefore defined;

(b) to prepare a compound of formula (I) wherein $R^1$ and $R^2$ are both hydrogen, reduction of a compound of formula (III):

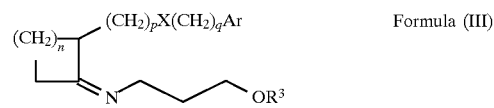

Formula (III)

wherein n, p, q, X and Ar are as hereinbefore defined and $R^3$ is $C_{1-4}$alkyl or phenyl$C_{1-4}$alkyl (e.g. benzyl);

(c) to prepare a compound wherein X is 0 or S reaction of a compound of formula (IV):

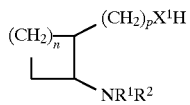

Formula (IV)

wherein $R^1$, $R^2$, p and n are as hereinbefore defined and $X^1$ is O or S, with a compound of formula $L(CH_2)_qAr$ wherein L is a leaving group and q and Ar are as hereinbefore defined;

(d) reaction of a compound formula (V):

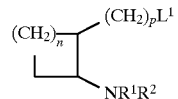

Formula (V)

wherein $R^1$, $R^2$, p and n are as hereinbefore defined and $L^1$ is a group displaceable by a nucleophile, with a compound $HX(CH_2)_qAr$ wherein X, q and Ar are as hereinbefore defined;

(e) interconversion of a compound of formula (I) to a different compound of formula (I), e.g.
  (i) where one of $R^1$ and $R^2$ is hydrogen and the other is alkyl, conversion to a compound of formula (I) wherein $R^1$ and $R^2$ are both alkyl, or
  (ii) where $R^1$ and $R^2$ are both hydrogen, conversion to a compound of formula (I) where at least one of $R^1$ and $R^2$ represent alkyl;
  (iii) conversion of a benzoyl substituent in the group Ar to benzyl, or to 1-methyl-1-phenylethyl; and optionally after any of the above processes, forming a salt of formula (I).

Process (a) may be effected using a suitable reducing agent such as sodium cyanoborohydride, preferably in an inert solvent such as tetrahydrofuran, methanol or diethyl ether.

Reduction of a compound of formula (III) according to process (b) may be effected using a reducing agent such as lithium borohydride and trimethylsilyl chloride, lithium aluminium hydride or $NaBH_3(OCOCF_3)$ in an inert solvent such as an ether, e.g. diethyl ether or tetrahydrofuran. In general this process gives predominantly the cis-form of the product.

In process (c) the reaction between a compound of formula (IV) and $L(CH_2)_qAr$ may be effected under conditions which depend on the nature of L and the value of q. For example when q is zero, L is preferably fluoro and the reaction is preferably effected in the presence of a strong base such as sodium hydride, and in a polar organic solvent such as dimethylsulphoxide or dimethylformamide. In this case the aryl group is preferably substituted by an activating group such as benzoyl. When q is other than zero, L may be for example halo or preferably a sulphonic acid residue such as a tosylate or mesylate and the reaction may be carried out using standard conditions, in a solvent and optionally in the presence of a base, which solvent and base may, if desired be selected from those described above.

The reaction between a compound of formula (V) and $HX(CH_2)_qAr$ in process (d) can take place under conditions which depend on the nature of $L^1$ and X. For example when $L^1$ is hydroxy, q is zero and X is oxygen or sulphur the reaction is carried out in the presence of diethyl azodicarboxylate and triphenyl phosphine. Such a reaction is known as the Mitsunobu reaction (as described in Synthesis 1981, 1; and J. Org. Chem. 1991, 56, 670–672). Alternatively the leaving group $L^1$ may be for example a halogen atom or a sulphonyloxy group eg. methane-sulphonyloxy or p-toluene sulphonyloxy in which case the reaction may be effected using standard conditions, in the presence or absence of solvent, optionally in the presence of a base.

Interconversions (i) and (ii) according to process (e) may be effected by alkylation of a compound (I) wherein one of $R^1$ and $R^2$ is hydrogen and the other is alkyl or where $R^1$ and $R^2$ are both hydrogen, using an appropriate alkylating agent such as an alkyl halide e.g. an alkyl bromide or iodide, in the presence of a base, such as potassium carbonate. The reaction may be carried out in a suitable solvent such as acetone. Alternatively said compound of formula (I) may first be acylated, using for example an alkylhaloformate such as ethyl chloroformate, preferably in the presence of a tertiary amine such as triethylamine, or a carbonate such as di-tert-butyldicarbonate, in the presence of sodium hydroxide and a solvent such as dioxane, to provide a compound of formula (VI):

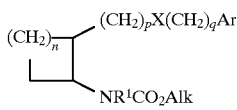

Formula (VI)

wherein n, p, q, X, Ar and $R^1$ are as hereinbefore defined and Alk is a $C_{1-4}$alkyl group; followed by reduction as described above. In a further method a compound of formula (I) may be subjected to reductive alkylation using an appropriate aldehyde (e.g. formaldehyde) or ketone, and a reducing agent such as sodium cyanoborohydride.

Reduction of a benzoyl substituent to benzyl according to (e)(iii) may be effected using e.g. sodium borohydride in trifluoroacetic acid. Conversion of the benzoyl group to a 1-methyl-1-phenethyl group can be effected by reaction with $(CH_3)_2TiCl_2$, for example in dichloromethane at $-40°$ C. (as generally described by Reetz et al. J. Org. Chem. 48 254 (1983)) and analogues can be prepared by variations of this method.

It will be appreciated that when any of the processes described herein involve a reduction step it will generally be desirable to employ reducing agents and conditions which do not affect or disturb substituents which are intended to be retained in the final product. The choice of appropriate reducing agents and conditions will be readily apparent to the skilled practitioner. Thus for example when Ar represents 3,4-dichlorophenyl it is preferable to avoid the use of lithium aluminium hydride under forcing (e.g. reflux) conditions.

If necessary during any of processes (c), (d) and (e)(iii) when $R^1$ and $R^2$ both represent hydrogen the amino group may be protected using standard methods e.g. as a phthalimido group which may be removed at the end of the synthesis by treatment with hydrazine.

Processes (c) and (e) generally proceed with retention of the cis or trans configuration of the starting material.

A compound of formula (II) may be prepared using standard procedures analogous to those outlined in DE 4010325.

A compound of formula (III) may be prepared by reaction of a compound of formula (VII):

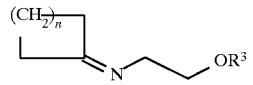

Formula (VII)

with a compound of formula $L^2(CH_2)_pX(CH_2)_qAr$ in the presence of lithium bis-(trimethylsilyl)amide in a solvent such as tetrahydrofuran.

Compounds of formula (IV) wherein X is O can be prepared using standard methods. For example the compound of formula (IV) in which n is 2, p is 1 and $R^1$ and $R^2$ are both hydrogen can be prepared by reduction, for example using lithium aluminium hydride, of the corresponding cis-2-amino-1-cyclopentane carboxylic acid which is commercially available.

When a compound of formula (I) is obtained as a mixture of enantiomers, these may be separated by conventional methods such as crystallisation in the presence of a resolving agent, or chromatography, for example using a chiral HPLC column.

An ischaemic event such as stroke results in disruption of the blood supply to the brain, depriving it of essential oxygen. A cascade of biochemical reactions ensues, a consequence of which is to permit the influx of calcium ions into the brain cells (neurons) via so-called Voltage Operated Calcium Channels (VOCCs) causing cell death. It is believed that agents which inhibit such calcium influx will minimise cell death and hence increase the potential for recovery.

Compounds of formula (I) have been found to exhibit high calcium influx blocking activity for example in neurons. As such the compounds are expected to be of use in therapy in treating conditions and diseases related to an accumulation of calcium in the brain cells of mammals, in particular humans. For example, the compounds are expected to be of use in the treatment of ischaemia including for example stroke, anoxia, and traumatic head injury. They may also be of use in the treatment of migraine, visceral pain, epilepsy, AIDS-related dementia, neurodegenerative diseases such as Alzheimer's disease and age-related memory disorders, mood disorders and drug addiction withdrawal such as ethanol addiction withdrawal.

In a further aspect of the invention there is therefore provided a method of treatment of conditions or diseases related to (e.g. caused or exacerbated by) the accumulation of calcium in the brain cells of mammals which comprises administering to a subject in need thereof an effective amount of a compound of formula (I) or a pharmaceutically acceptable salt thereof. Thus, for example, the present invention provides a method of treatment of ischaemia including for example stroke, anoxia or traumatic head injury which comprises administering to a subject in need thereof, an effective amount of a compound of formula (I) or a pharmaceutically acceptable salt thereof. The invention also provides a method of treatment of migraine, visceral pain, epilepsy, AIDS-related dementia, neurodegenerative diseases such as Alzheimer's disease, and age-related memory disorders, mood disorders and drug addiction withdrawal such as ethanol addiction withdrawal, which comprises administering to a subject in need thereof, an effective amount of a compound of formula (I) or a pharmaceutically acceptable salt thereof.

The present invention also provides the use of a compound of formula (I) or a pharmaceutically acceptable salt thereof in the manufacture of a medicament for the treatment of a condition or disease related to the accumulation of calcium in the brain cells of a mammal.

Compounds of the present invention will preferably be of use in the treatment of ischaemic stroke.

For use in medicine, the compounds of formula (I) are usually administered in a standard pharmaceutical composition. The present invention therefore provides in a further aspect pharmaceutical compositions comprising a novel compound of formula (I) or a pharmaceutically acceptable salt thereof and a pharmaceutically acceptable carrier or excipient.

The compounds of formula (I) may be administered by any convenient method for example by oral, parenteral, buccal, rectal or transdermal administration and the pharmaceutical compositions adapted accordingly.

The compounds of formula (I) and their pharmaceutically acceptable salts which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compounds of the invention may also be administered parenterally, by bolus injection or continuous infusion. Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Both liquid and solid compositions may contain other excipients known in the pharmaceutical art, such as cyclodextrins.

Preferably the composition is in unit dose form such as a tablet, capsule or ampoule.

Each dosage unit for oral administration contains preferably from 1 to 250 mg (and for parenteral administration contains preferably from 0.1 to 60 mg) of a compound of the formula (I) or a pharmaceutically acceptable salt thereof calculated as the free base.

The daily dosage regimen for an adult patient may be, for example, an oral dose of between 1 mg and 500 mg, preferably between 1 mg and 250 mg, e.g. 5 to 200 mg or an intravenous, subcutaneous, or intramuscular dose of between 0.1 mg and 100 mg, preferably between 0.1 mg and 60 mg, e.g. 1 to 40 mg of the compound of the formula (I) or a pharmaceutically acceptable salt thereof calculated as the free base, the compound being administered 1 to 4 times per day. Alternatively the compounds of the invention may be administered by continuous intravenous infusion, preferably at a dose of up to 400 mg per day. Thus, the total daily dosage by oral administration will be in the range 1 to 2000 mg and the total daily dosage by parenteral administration will be in the range 0.1 to 400 mg. Suitably the compounds will be administered for a period of continuous therapy, for example for a week or more. It will be appreciated that the precise dosage and timing will be at the discretion of the physician and will depend amongst other factors on the severity of the condition to be treated. However, in general the first dose of a compound of the invention will preferably be administered as soon as possible following an ischaemic event, eg within 12 hours, preferably within 6 hours.

If desired a compound of formula (I) or a pharmaceutically acceptable salt thereof may be administered in combination or concurrently with one or more other therapeutic agents, for example a thrombolytic agent such as anistreplase, streptokinase or a tissue plasminogen activator; an excitatory amino acid antagonist such as an NMDA antagonists; a free radical inhibitor; or a calpain inhibitor.

BIOLOGICAL DATA $Ca^{2+}$ Current Measurement

Cell preparations

Sensory neurons from dorsal root ganglia were dissociated from 1 day old rat pups (Forda et al, Developmental Brain Research, 22 (1985), 55–65). Cells were plated out onto glass coverslips and used within 3 days to permit effective voltage clamp of $Ca^{2+}$ currents. Superior cervical ganglion neurons were isolated and cultured following a method modified from Marrion et al, Neurosci. Lett., 77, 55–60 (1987). Cells were plated onto laminin coated plastic tissue culture dishes and incubated at 37° C. until just prior to recording. Electrophysiological recordings were performed from 2 to 9 days after dissociation.

Solutions

The pipette (internal solution) contained in mM: CsCl, 130; HEPES, 10; EGTA, 10; $MgCl_2$, 4; ATP, 2; buffered to pH 7.2 with CsOH. Cells were bathed in a normal Tyrodes solution before establishment of whole cell recording when the bathing solution was changed to one allowing isolation of $Ca^{2+}$ currents. The external solution for recording $Ca^{2+}$ channel currents contained in mM: $BaCl_2$, 10; TEA-Cl, 130; glucose, 10; HEPES, 10; $MgCl_2$, 1; buffered to pH 7.3 with TEA—OH. Barium was used as the charge carrier as this assists in current isolation and calcium dependent inactivation of current is avoided. Compounds were dissolved in DMSO to make a 20 mM stock solution. At the drug concentration used the vehicle (0.1%) had no significant effect on $Ca^{2+}$ currents. All experiments were performed at 21° to 24° C. Whole cell currents were recorded using List EPC-7 amplifiers and stored, digitised for later analysis using PC based software similar to that described previously (Benham & Tsien, Journal of Physiology (1988), 404, 767–784).

$Ca^{2+}$ currents

Peak voltage gated $Ca^{2+}$ channel currents of up to 10 nA from dorsal root ganglion neurons were recorded using 10 mM $Ba^{2+}$ as charge carrier. Currents were evoked from a holding potential of −80 mV to a test potential of 0 or +10 mV every 15 seconds. This test potential was at the peak of the current voltage relationship and assessing block at this point reduced any errors due to drifting holding potential. Some cells showed slow rundown of current as is commonly seen when recording $Ca^{2+}$ currents. The rundown rate was measured in control conditions and extrapolated through the time of drug application to derive a rundown corrected control value.

RESULTS

Dorsal Root Ganglion Cells

Block by 20 $\mu$M drug was assessed 3 minutes after drug application. In this test compounds of Examples 1–3 and 5–7 gave percentage inhibition of plateau $Ca^{2+}$ current in the range 69–90% at 20 $\mu$M.

Superior Cervical Ganglion Cells

Once a constant calcium current had been recorded for 4 successive pulses (1 minute) 10 $\mu$M Nimodipine, a dihydropyridine, was applied to the cell to block L type calcium current. After three minutes 5 $\mu$M drug was coapplied with 10 $\mu$M Nimodipine for three minutes. Such drug application tested the block of the remaining, predominantly N type, calcium current. In this test compounds of Examples 1–3 and 5–13 gave percentage inhibition of plateau $Ca^{2+}$ current in the range 38 to 94% at 5 $\mu$M.

PHARMACEUTICAL FORMULATIONS

The following represent typical pharmaceutical formulations according to the present invention, which may be prepared using standard methods.

IV Infusion

| Compound of formula (I) | 1–40 mg |
|---|---|
| Buffer | to pH ca 7 |
| Solvent/complexing agent | to 100 ml |

Bolus Injection

| Compound of formula (I) | 1–40 mg |
|---|---|
| Buffer | to pH ca 7 |
| Co-Solvent | to 5 ml |

Buffer: Suitable buffers include citrate, phosphate, sodium hydroxide/hydrochloric acid.

Solvent: Typically water but may also include cyclodextrins (1–100 mg) and co-solvents such as propylene glycol, polyethylene glycol and alcohol.

Tablet

| Compound | 1–40 mg |
|---|---|
| Diluent/Filler* | 50–250 mg |
| Binder | 5–25 mg |
| Disintegrant* | 5–50 mg |
| Lubricant | 1–5 mg |
| Cyclodextrin | 1–100 mg |

*may also include cyclodextrins

Diluent: e.g. Microcrystalline cellulose, lactose, starch

Binder: e.g. Polyvinylpyrrolidone, hydroxypropymethylcellulose

Disintegrant: e.g. Sodium starch glycollate, crospovidone

Lubricant: e.g. Magnesium stearate, sodium stearyl fumarate.

Oral Suspension

| Compound | 1–40 mg |
|---|---|
| Suspending Agent | 0.1–10 mg |
| Diluent | 20–60 mg |
| Presevative | 0.01–1.0 mg |
| Buffer | to pH ca 5–8 |
| Co-solvent | 0–40 mg |
| Flavour | 0.01–1.0 mg |
| Colourant | 0.001–0.1 mg |

Suspending agent : e.g. Xanthan gum, microcrystalline cellulose

Diluent: e.g. sorbitol solution, typically water

Preservative: e.g. sodium benzoate

Buffer: e.g. citrate

Co-solvent: e.g. alcohol, propylene glycol, polyethylene glycol, cyclodextrin

The invention is further illustrated by the following non-limiting Preparations and Examples:

PREPARATION 1

(±) 2-(4-Benzyloxyphenoxy)-cyclopentanone

To a mixture of 4-benzyloxyphenol (5 g, 25 mmol), potassium iodide (125 mg), and potassium carbonate (4.48 g, 32.5 mmol) in 2-butanone (30 ml) was added 2-chlorocyclopentanone (5.9 g, 50 mmol). The mixture was heated at reflux for 5 h, filtered and concentrated in vacuo. The residue was dissolved in diethyl ether and washed successively with 10% aqueous sodium hydroxide, water and brine. After drying over magnesium sulfate, solvents were removed in vacuo and the residue subjected to flash chromatography on silica gel eluting with 30% diethyl ether in hexanes to afford the title compound as a pale orange solid (2.4 g).

$^1$H Nmr (CDCl$_3$) δ: 1.94 (2H, m), 2.15 (1H, m), 2.39 (3H, m), 4.49 (1H, t, J=7 Hz), 5.01 (2H, s), 6.92 (4H, m), 7.37 (5H, m).

PREPARATION 2

(±) 2-(4-Benzyloxybenzyl)cyclopentanone oxime-o-benzyl ether

To a solution of lithium bis-(trimethylsilyl)amide (34 ml of a 1M solution in tetrahydrofuran, 34 mmol ) in dry tetrahydrofuran (80 ml) at −780° C. under nitrogen was added a solution of cyclopentanone oxime-o-benzyl ether (5.72 g, 30.2 mmol) in tetrahydrofuran (25 ml). After 10 minutes a solution of 4-benzyloxybenzyl chloride (7.78 g; 33.4 mmol) in tetrahydrofuran (25 ml) was added in one portion and the cooling bath removed. When the reaction mixture had reached room temperature, stirring was continued overnight before pouring into a large excess of water and extracting with diethyl ether (3×50 ml). The combined organic extracts were dried over sodium sulfate and volatiles removed in vacuo. The residue was subjected to column chromatography on silica gel eluting with 5% diethyl ether in hexanes to afford the title compound as a yellow oil (3.87 g).

$^1$H Nmr (CDCl$_3$) δ: 1.31–1.92 (10H, m), 2.51 (1H, dd, J=8 and J=14 Hz), 2.73 (1H, dd, J=6 Hz and J=14 Hz), 5.04 (2H, s), 6.87 (2H, d, J=8 Hz), 7.10 (2H, d, J=8 Hz), 7.35 (5H, m).

PREPARATION 3

(±) cis-1-(4-Benzyloxybenzyl)-2-tert-butoxycarbonylaminocyclopentane (±) cis-1-(4-Benzyloxybenzyl)-2-aminocyclopentane (470 mg, 1.7 mmol) was dissolved in dioxane (25 ml) and cooled to 0° C. Aqueous 3M NaOH (560 μl) and di-tert-butyldicarbonate (397 μl, 1.7 mmol) were added, and the reaction stirred at room temperature for 3 h before pouring into water and extracting with diethyl ether (3×40 ml). After drying over sodium sulfate, solvents were removed in vacuo and the residue recrystallised from ethanol/ hexanes to afford the title compound as an off white solid.

PREPARATION 4

(±) cis-1-Amino-2-hydroxymethylcyclopentane

To a suspension of lithium aluminium hydride (3.68 g, 0.097 mol) in dry tetrahydrofuran (250 ml) under argon was added portionwise (±) cis-2-amino-1-cyclopentanecarboxylic acid (2.50 g, 0.019 mol) . After stirring overnight at room temperature the reaction was quenched with wet diethyl ether followed by a minimum amount of water. The aluminium salts were removed by filtration and the precipitate was washed with 5% methanol in diethyl ether. The combined filtrate and washings were concentrated in vacuo to give an oil (1.9 g) which was distilled on a Kugelrohr apparatus (150° C. at 0.3 mm Hg) to give the title compound as a colourless oil (1.74 g).

PREPARATION 5

(±) cis 1-Ethoxycarbonylamino-2-(4-benzylphenoxymethyl)cyclopentane

To a solution of (±) cis 1-amino-2-(4-benzylphenoxymethyl)cyclopentane (0.9 g, 3.20 mmol) in dry diethyl ether (100 ml) containing triethylamine (0.89 ml, 6.4 mmol) was added ethyl chloroformate (0.40 ml, 4.16 mmol) under argon. After stirring at room temperature for 2.5 h the reaction was quenched with ice water and the pH of the aqueous layer was adjusted to 7 by addition of dilute hydrochloric acid. The organic layer was separated and the aqueous phase was extracted with diethyl ether (2×50 ml). The combined organic layers were washed with brine, dried over sodium sulfate and concentrated in vacuo to give a pale yellow oil (1.16 g) which was used in the next stage without further purification.

PREPARATION 6

(±) cis-1-Hydroxymethyl-2-phthalimidocyclopentane

A mixture of (±) cis 1-amino-2-hydroxymethylcyclopentane (0.59 g, 5.1 mmol) and phthalic anhydride (0.76 g, 5.1 mmol) in xylene (40 ml) was heated under argon at reflux using a condenser fitted with a Dean and Stark trap. After 1.5 h the reaction was concentrated in vacuo and the residue was purified by column chromatography on silica gel eluting with diethyl ether to give the title compound as a pale yellow oil (1.0 g).

$^1$H Nmr (CDCl$_3$) δ: 1.52–1.95 (3H, m), 1.98–2.20 (3H, m), 2.28–2.55 (2H, m), 3.45 (1H, m), 3.60 (1H, m), 4.75 (1H, q, J=7 Hz), 7.25 (2H, m), 7.30 (2H, m).

PREPARATION 7

(±) cis-1-[4-(1-Methyl-1-phenylethyl) phenoxymethyl]-2-phthalimidocyclopentane

To an ice cold solution of (±) cis-1-hydroxymethyl-2-phthalimidocyclopentane (1.0 g, 4.08 mmol), triphenylphosphine (1.28 g, 4.9 mmol) and 4-cumylphenol (1.04 g, 4.9 mmol) in dry tetrahydrofuran (40 ml) was added diethyl azodicarboxylate (0.77 ml, 4.9 mmol). The mixture was allowed to warm to room temperature and stirred for 48 h. The reaction was poured into ice water (200 ml) and extracted into diethyl ether (3×100 ml). The combined extracts were washed with brine, dried over sodium sulfate and concentrated in vacuo. The resulting crude product was purified by chromatography on a silica gel column eluting with 10–40% diethyl ether in petroleum ether 40–60. Pooling of pure fractions afforded the title compound as a colourless oil (0.48 g). Additional fractions afforded a further 0.76 g of product which was slightly contaminated with 4-cumylphenol.

$^1$H Nmr (CDCl$_3$) δ: 1.45–2.16 (6H, s and 5H, m), 2.45–2.78 (2H, m), 3.88 (2H, m), 4.88 (1H, q, J=8 Hz), 6.48 (1H, d, J=9 Hz), 6.92 (2H, d, J=9 Hz), 7.08–7.30 (5H, m), 7.58–7.78 (4H, m)

PREPARATION 8

(±) cis-1-Ethoxycarbonylamino-2-[4-(1-methyl-1-phenylethyl)phenoxymethyl] cyclopentane To a solution of (±) cis-1-amino-2-[4-(1-methyl-1-phenylethyl)phenoxymethyl] cyclopentane (0.35 g, 1.13 mmol) in dry diethyl ether (30 ml) containing triethylamine (0.31 ml, 2.26 mmol) was added a solution of ethyl chloroformate (0.18 g, 1.70 mmol) in diethyl ether (5 ml). The reaction was stirred at room temperature for 2 h and then poured into ice-water. The pH of the aqueous phase was adjusted to approximately 7 by the addition of dilute hydrochloric acid. The aqueous layer was separated and extracted with diethyl ether (2×30 ml). The combined organic layers were washed with water followed by brine, then dried over sodium sulfate and concentrated in vacuo to give an oil (0.41 g) which was used in the next stage without purification.

PREPARATION 9

4-[1-(4-Fluorophenyl)-1-methylethyl]phenyl methyl ether

To a solution of titanium tetrachloride (40 ml of a 1M solution in dichloromethane, 40 mmol) cooled to −40° C. under argon was added dimethylzinc (20 ml of a 2M solution in toluene, 40 mmol), and the mixture was stirred for 10 minutes. A solution of 4-fluoro-4-methoxybenzophenone (4.18 g, 18.2 mmol) in dichloromethane (20 ml) was added whilst maintaining the temperature between −30° C. and −40° C. The mixture was then allowed to warm to room temperature and stirred for 72 h. The reaction was poured into to ice cold water (100 ml) and the aqueous phase extracted with diethyl ether (3×30 ml). The combined organic phases were washed with sodium hydrogen carbonate followed by brine, then dried over sodium sulfate. After concentration in vacuo the residue was subjected to column chromatography on silica gel eluting with 5% diethyl ether in 40–60 petroleum ether to afford the title compound as an oil (3.34 g).

$^1$H Nmr (CDCl$_3$) δ: 1.64 (6H, s), 3.78 (3H, s), 6.80 (2H, d, J=9 Hz), 6.92 (2H, t, J=9 Hz), 7.10–7.22, 4H, m).

PREPARATION 10

4-[1-(4-Fluorophenyl)-1-methylethyl]phenol

To a solution of 4-[1-(4-fluorophenyl)-1-methylethyl] phenyl methyl ether (3.34 g, 13.67 mmol) in chloroform (40 ml) was added trimethylsilyl iodide (4.10 g, 20.51 mmol). The solution was stirred under argon at 40° C. for 18 h, then cooled and poured into ice cold water (50 ml). The aqueous phase was extracted with chloroform (6×20 ml), and the combined organic layers were washed with sodium metabisulfite then brine, and dried over sodium sulfate. After concentration in vacuo the residue was subjected to column chromatography on silica gel eluting with 10–40% diethyl ether in 40–60 petroleum ether to afford the title compound as an oil (2.4 g).

$^1$H Nmr (CDCl$_3$) δ: 1.64 (6H, s), 4.81 (1H, s), 6.74 (2H, d, J=9 Hz), 6.93 (2H, t, J=9 Hz), 7.08 (2H, d, J=9 Hz), 7.18 (2H, m).

PREPARATION 11

(±) cis-1-[4-(1-(4-Fluorophenyl)-1-methylethyl) phenoxymethyl-2-phthalimido cyclopentane To an ice cold solution of (±) cis-1-hydroxymethyl-2-phthalimidocyclopentane(1.17 g, 4.78 mmol), triphenylphosphine (1.50 g, 5.74 mmol) and 4-[1-(4-fluorophenyl)-1-methylethyl]phenol (1.1 g, 4.78 mmol) in dry tetrahydrofuran (40 ml) was added diethyl azodicarboxylate (0.90 ml, 5.74 mmol). The mixture was allowed to warm to room temperature and stirred for 4 days. The reaction was worked up as described in Preparation 7. The resulting yellow foam was purified by chromatography on a silica gel column eluting with 20–40% diethyl ether in petroleum ether 40–60. Pooling of pure fractions afforded the title compound as a colourless oil (0.61 g). Additional fractions afforded a further 0.9 g of product which was slightly contaminated with 4-[1-(4-fluorophenyl)-1-methylethyl]phenol.

$^1$H Nmr (CDCl$_3$) δ: 1.45–2.14 (6H, s and 5H, m), 2.43–2.78 (2H, m), 3.88 (2H, m), 4.88 (1H, q, J =8 Hz), 6.48 (2H, d, J=9 Hz), 6.90 (4H, m), 7.05 (2H, m), 7.60–7.78 (4H, m)

PREPARATION 12

(±) cis-1-Ethoxycarbonylamino-2-[4-(1-(4-fluorophenyl)-1-methylethyl)phenoxymethyl] cyclopentane To a solution of (±) cis -1-amino-2-[4-(1-(4-fluorophenyl) -1-methylethyl)phenoxymethyl] cyclopentane (0.58 g, 1.77 mmol) in dry diethyl ether (30 ml) containing triethylamine (0.49 ml, 3.54 mmol) was added a solution of ethyl chloroformate (0.29 g, 2.66 mmol) in diethyl ether (5 ml). The reaction was worked up as described in Preparation 8, and the resulting yellow oil (0.62 g) was used directly in the next stage.

EXAMPLES 1 and 2

(±) 1-Methylamino-2-(4-benzyloxyphenoxy) cyclopentane Hydrochloride (cis and trans)

To a solution of 2-(4-benzyloxyphenoxy)cyclopentanone (1.76 g, 6.2 mmol) in methanol (150 ml) was added methylamine hydrochloride (2.09 g, 31 mmol) and sodium cyanoborohydride (390 mg, 6.2 mmol) and the mixture stirred overnight at room temperature. The reaction mixture was concentrated in vacuo then partitoned between diethyl ether and aqueous sodium bicarbonate. The organic phase was dried over sodium sulfate and concentrated in vacuo. The cis and trans diastereomers were separated by column chromatography on silica gel, eluting with 5% ethanol in chloroform and the corresponding HCl salts prepared.

More polar diastereomer (E1), m.p 149°–150° C. (from methanol/diethyl ether) $^1$H Nmr (DMSO-d$_6$) δ: 2.13 (1H, m), 2.56 (3H, s), 3.51 (1H, m), 4.76 (1H, m), 5.06 (2H, s), 6.99 (4H, m), 7.41 (5H, m), 9.15 (2H, br. s).

Less polar diastereomer (E2), m.p. 122.5°–123.5° C. (from methanol/diethyl ether) $^1$H Nmr (DMSO-d$_6$) δ: 1.76 (4H, m), 2.17 (2H, m), 2.59 (3H, s), 3.52 (1H, m), 4.85 (1H, m), 5.05 (2H, s), 6.95 (4H, m), 7.39 (5H, m), 9.45 (2H, br. s).

EXAMPLE 3

(±) cis-1-methylamino-2-(4-Benzyloxybenzyl) cyclopentane Hydrochloride (E3)

To a solution of lithium aluminium hydride (445 mg, 12 mmol) in dry tetrahydrofuran (25 ml) under nitrogen was added dropwise a solution of (±) cis-1-(4-benzyloxybenzyl) -2-tert-butoxycarbonylaminocyclopentane (446 mg, 1.2 mmol) in dry tetrahydrofuran (25 ml). The reaction was heated at reflux for 3 h then cooled with an ice/water bath and quenched with the minimum of water. The reaction was filtered and dried over sodium sulfate. Solvents were removed in vacuo and the residue subjected to column chromatography on silica gel eluting with 10% ethanol in chloroform to afford a colourless oil (146 mg) which was converted to the HCl salt and crystallised to afford the title compound as a white solid, m.p. 183°–184° C. (from methanol/diethyl ether).

$^1$H Nmr (DMSO-d$_6$) δ: 1.28 (1H, m), 1.62 (4H, m), 1.97 (1H, m), 2.20 (1H, m), 2.37 (1H, m), 2.50 (3H, s), 2.94 (1H, dd, J=5 Hz and J=15 Hz), 3.10 (1H, m), 5.07 (2H, s), 6.93 (2H, d, J=8 Hz), 7.16 (2H, d, J=8 Hz), 7.40 (5H, m), 8.97 (2H, br. s).

EXAMPLE 4

(±) cis-1-amino-2-(4-Benzyloxybenzyl)cyclopentane (E4)

To a solution of lithium aluminium hydride (312 mg, 8.2 mmol) in dry diethyl ether (30 ml) was added dropwise a solution of (±) 2-(4-benzyloxybenzyl) cyclopentanone oxime-o-benzyl ether (500 mg, 1.4 mmol) in diethyl ether (30 ml). The mixture was allowed to stir at room temperature for 18 h before careful addition of a minimum amount of water to quench the reaction. The precipitated aluminium salts were filtered off and solvents removed in vacuo. The residue was subjected to column chromatography on silica gel eluting with 5% ethanol in choroform to afford the title compound as a yellow oil (240 mg).

$^1$H Nmr (CDCl$_3$) δ: 1.62 (4H, m), 2.30 (2H, m), 2.59 (1H, m), 3.12 (2H, m), 5.02 (2H, s), 5.12 (2H, s), 6.87 (2H, d, J=8 Hz), 7.06 (2H, d, J=8 Hz), 7.35 (10H, m).

EXAMPLE 5

(±) cis-1-Amino-2-(4-benzoylphenoxymethyl) cyclopentane Hydrochloride (E5)

A solution of (±) cis-1-amino-2-hydroxymethylcyclopentane (1.1 g, 0.01 mol) in dry dimethyl sulfoxide (20 ml), was treated with sodium hydride (0.36 g of an 80% dispersion in oil; 0.012 mol). After stirring for 2.5 h at room temperature under argon a solution of 4-fluorobenzophenone (2.2 g, 0.011 mol) in dry dimethyl sulfoxide (10 ml) was added dropwise. The mixture was warmed slowly to 50°–60° C. and held at this temperature for 15 min. The reaction was quenched at ice temperature with glacial acetic acid (0.69 ml, 0.012 mol) and then concentrated in vacuo using co-distillation with xylene. The residue was partitioned between water (100 ml) and diethyl ether (200 ml). The aqueous layer was basified with potassium carbonate and further extracted with diethyl ether (3×200 ml). The combined organic layers were dried over sodium sulfate and then concentrated in vacuo to give an oil. Purification by chromatography on silica gel eluting with 0–20% methanol in diethyl ether afforded a light brown oil (2.4 g). Treatment with ethereal HCl produced the hydrochloride salt which was recrystallised twice to give the title compound as a colourless solid. m.p. 182°–185° C. (from methanol/diethyl ether).

$^1$H Nmr (CDCl$_3$) δ: 1.45–2.10 (6H, m), 2.49 (1H, m), 3.42 (1H, br m), 4.10 (1H, dd, J=10 Hz and J=7 Hz), 4.25 (1H, dd, J=10 Hz and J=8 Hz), 7.05 (2H, d, J=9 Hz), 7.35–7.90 (7H, m), 8.30 (3H, br s).

EXAMPLE 6

(±) cis-1-Amino-2-(4-benzylphenoxymethyl) cyclopentane Hydrochloride (E6)

A solution of (+) cis-1-amino-2-(4-benzoylphenoxymethyl)cyclopentane (2.0 g, 6.78 mmol) in dichloromethane (30 ml) containing trifluoroacetic acid (40 ml) was cooled in ice in an argon atmosphere and treated with a pellet of sodium borohydride (0.4 g). After 1 h a second pellet of sodium borohydride (0.4 g) was added. The mixture was left stirring overnight at room temperature and then treated with a third pellet of sodium borohydride. After a further 6 h the reaction was cooled in ice, treated with water and then basified with sodium hydroxide pellets. The mixture was extracted into diethyl ether and the combined extracts were concentrated in vacuo to give a brown oil. Purification on silica gel eluting with 10–20% methanol in diethyl ether afforded a light brown oil (1.3 g). Extraction into pentane followed by treatment with ethereal HCl afforded the hydrochloride salt which was crystallised to give the title compound as a colourless solid. m.p. 181°–183° C. (from methanol/diethyl ether).

$^1$H Nmr (CDCl$_3$) δ: 1.30–1.90 (6H, m), 2.25 (1H, m), 3.24 (1H, br m), 3.86 (2H, s), 3.92 (1H, dd, J=10 Hz and J=6 Hz), 4.08 (1H, dd, J=10 Hz and J=7 Hz), 6.92 (2H, d, J=9 Hz), 7.03 (2H, d, J=9 Hz), 7.10–7.30 (5H, m), 8.20 (3H, br s).

EXAMPLE 7

(±) cis 1-Methylamino-2-(4-benzylphenoxymethyl) cyclopentane Hydrochloride (E7)

To a suspension of lithium aluminium hydride (0.65 g, 17.0 mmol) in dry diethyl ether (75 ml) under argon was added dropwise a solution of (±) cis 1-ethoxycarbonylamino-2-(4-benzylphenoxymethyl) cyclopentane (1.13 g, 3.2 mmol) in dry diethyl ether (25 ml). After stirring overnight at room temperature the reaction was quenched with wet diethyl ether followed by a minimum amount of water. The aluminium salts were removed by filtration and the filtrate was concentrated in vacuo to give a pale yellow oil (0.93 g). Extraction into pentane followed by treatment with ethereal HCl afforded the hydrochloride salt which was crystallised to give the title compound as a colourless solid. m.p. 183°–185° C. (from methanol/diethyl ether).

$^1$H Nmr (CDCl$_3$) δ: 1.50–2.20 (6H, m), 2.60 (overlapping signals: 3H, s and 1H, m), 3.43 (1H, m), 3.90 (2H, s), 4.05 (1H, dd, J=10 Hz and J=7 Hz), 4.30 (1H, dd, J=10 Hz and J=7 Hz), 6.80–7.35 (7H, m), 9.02 (1H, br s), 9.53 (1H, br s).

EXAMPLE 8

(±) cis-1-Amino-2-(3,4-dichlorophenoxymethyl) cyclopentane Hydrochloride (E8)

A solution of (±) cis-1-amino-2-hydroxymethylcyclopentane (0.67 g, 5.82 mmol) in dry dimethyl sulfoxide (20 ml), was treated with sodium hydride (0.21 g of an 80% dispersion in oil; 7.0 mmol). After stirring for 3.25 h at room temperature under argon 1,2-dichloro-4-fluorobenzene (0.83 ml, 7.0 mmol) was added dropwise. After stirring at room temperature for 24 h the mixture was quenched at ice temperature with glacial acetic acid (0.4 ml) and then worked up as described in Example 5. Purification by chromatography on silica gel eluting with 0–20% methanol in diethyl ether afforded a light brown oil (1.15 g). Extraction into a mixture of diethyl ether and hexane followed by treatment with ethereal HCl produced the hydrochloride salt which was recrystallised to give the title compound as a colourless solid. m.p. 264°–265° C. (dec) (from methanol/diethyl ether).

$^1$H Nmr (DMSO-d$_6$) δ: 1.46–2.10 (6H, m), 2.45 (1H, m), 3.60 (1H, m), 4.02 (1H, dd, J=10 Hz and J=8 Hz), 4.14 (1H, dd, J=10 Hz and J=8 Hz), 7.00 (1H, dd, J=8 Hz and J=2 Hz), 7.26 (1H, d, J=2 Hz), 7.55 (1H, d, J=8 Hz), 8.19 (3H, br s).

EXAMPLE 9

(±) cis-1-Amino-2-[4-(4-fluorophenoxy) phenoxymethyl]cyclopentane hydrochloride

A solution of (±) cis-1-amino-2-hydroxymethylcyclopentane (0.46 g, 4.0 mol) in dry dimethyl sulfoxide (12 ml), was treated with sodium hydride (0.144 g of an 80% dispersion in oil; 4.8 mmol). After stirring for 3 h at room temperature under argon a solution of bis-(4-fluorophenyl)-ether (1.65g, 8.0 mmol) in dimethyl sulfoxide (2 ml) was added. The mixture was heated to 60° C. and held at this temperature for 19 h. The reaction was quenched at ice temperature with glacial acetic acid (0.27 ml, 4.8 mmol) and then worked up as described in Example 5. Purification by chromatography on silica gel eluting with 0–5% ethanol in diethyl ether afforded an oil. The product was extracted into diethyl ether-hexane, and insoluble impurities were discarded. Treatment with ethereal HCl produced the hydrochloride salt which was crystallised to give the title compound as a white solid (0.56 g) m.p. 170°–171° C. (from methanol/diethyl ether).

$^1$H Nmr (DMSO-d$_6$) δ: 1.50–2.10 (6H, m), 2.47 (1H, m), 3.63 (1H, m), 3.97 (1H, m), 4.12 (1H, m), 6.96 (6H, m), 7.18 (2H, m), 8.18 (3H, br s)

EXAMPLE 10

(±) cis-1-Amino-2-[4-(1-methyl-1-phenylethyl) phenoxymethyl]cyclopentane hydrochloride A mixture of (±) cis 1-[4-(1-methyl-1-phenylethyl) phenoxymethyl]-2-phthalimidocyclopentane (0.75 g, 1.70 mmol), hydrazine hydrate (0.25 g, 5.1 mmol), 2-propanol (25 ml) and methanol (25 ml) was heated at reflux under argon for 18 h. The reaction was concentrated in vacuo and the residue was partitioned between saturated sodium hydrogen carbonate (20 ml) and dichloromethane (20 ml). The aqueous layer was further extracted with dichloromethane (2×20 ml) and the combined organic layers were dried over sodium sulfate and concentrated in vacuo. Purification by column chromatography on silica gel eluting with 5% methanol in dichloromethane afforded an oil (0.35 g) which was converted into the hydrochloride salt and crystallised to give the title compound as a pale yellow solid m.p. 153°–156° C. (from methanol/diethyl ether).

$^1$H Nmr (DMSO-d$_6$) δ: 1.50–2.10 (6H, s and 6H, m), 2.45 (1H, m), 3.60 (1H, m), 3.96 (1H, m), 4.08 (1H, m), 6.85 (2H, d, J=9 Hz), 7.06–7.32 (7H, m), 8.10 (3H, br s).

EXAMPLE 11

(±) cis 1-Methylamino-2-[4-(1-methyl-1-phenylethyl)phenoxymethyl]cyclopentane hydrochloride To a suspension of lithium aluminium hydride (0.205 g, 5.38 mmol) in dry diethyl ether (10 ml) under argon was added dropwise a solution of (+) cis-1-ethoxycarbonylamino-2-[4-(1-methyl-1-phenylethyl) phenoxymethyl] cyclopentane. (0.41 g, 1.08 mmol) in dry diethyl ether (15 ml). After stirring overnight at room temperature the reaction was worked up as described in Example 7 to give a colourless oil (0.34 g) which was converted into the hydrochloride salt and crystallised twice to give the title compound as a colourless solid (0.27 g) m.p. 129°–131° C. (from acetone/diethyl ether).

$^1$H Nmr (DMSO-d$_6$) δ: 1.50–1.90 (6H, s and 5H, m), 2.02 (1H, m), 2.57 (3H, s and 1H, m), 3.50 (1H, m), 3.98 (1H, m), 4.12 (1H, m), 6.88 (1H, d, J=9 Hz), 7.08–7.30 (7H, m), 8.90 (2H, br d)

EXAMPLE 12

(±) cis-1-Amino-2-[4-(1-(4-fluorophenyl)-1-methylethyl)phenoxymethyl] cyclopentane hydrochloride A mixture of (±) cis-1-[4-(1-(4-fluorophenyl)-1-methylethyl)phenoxymethyl-2-phthalimido cyclopentane (1.5 g, 3.28 mmol), hydrazine hydrate (0.50 g, 9.8 mmol), 2-propanol (20 ml) and methanol (50 ml) was heated at reflux under argon for 24 h. The reaction was worked up as described in Example 10. Purification by column chromatography on silica gel eluting with 10–20% methanol in ethyl acetate afforded a colourless oil (0.78 g) which crystallised on cooling. Treatment with ethereal HCl afforded the title compound as a white solid m.p. 164.5°–165.5° C. (from methanol/diethyl ether)

$^1$H Nmr (DMSO-d$_6$) δ: 1.50–2.05 (6H, s, and 6H, m), 2.48 (1H, m), 3.60 (1H, m), 3.98 (1H, m), 4.10 (1H, m), 6.88 (2H, d, J=9 Hz), 7.00–7.30 (6H, m), 8.18 (3H, br s).

EXAMPLE 13

(±) cis-1-Methylamino-2-[4-(1-(4-fluorophenyl)-1-methylethyl)phenoxymethyl] cyclopentane hydrochloride To a suspension of lithium aluminium hydride (0.29 g, 7.7 mmol) in dry diethyl ether (10 ml) under argon was added dropwise a solution of (±) cis-1-ethoxycarbonylamino2-[4-(1-(4-fluorophenyl)-1-methylethyl)phenoxymethyl] cyclopentane. (0.62 g, 1.55 mmol) in dry diethyl ether (15 ml). After stirring overnight at room temperature the reaction was worked up as described in Example 7 to give an oil which was converted into the hydrochloride salt and crystallised to give the title compound as a white solid (0.49 g) m.p. 160°–161° C. (from methanol/diethyl ether).

$^1$H Nmr (DMSO-d$_6$) δ: 1.50–1.90 (6H, s and 5H, m), 2.00 (1H, m), 2.54 (3H, s and 1H, m), 3.52 (1H, m), 3.92 (1H, m), 4.14 (1H, m), 6.90 (2H, d, J=9 Hz), 7.00–7.30 (6H, m), 8.98 (2H, br d).

We claim:

1. A compound of formula (IA):

$$\begin{array}{c}(CH_2)_n\end{array} \diagup \begin{array}{c}(CH_2)_pX(CH_2)_qAr\\ \\ NR^1R^2\end{array} \qquad \text{Formula (IA)}$$

wherein

X is O, S, C=O or a bond;

p and q are independently 0–4;

$R^1$ and $R^2$ are each independently selected from the group consisting of hydrogen, $C_{1-6}$alkyl $C_{3-6}$cycloalkyl or $C_{3-6}$cycloalkyl$C_{1-4}$alkyl;

n is 1, 2, 3 or 4; and

Ar is phenyl optionally substituted by 1 to 3 substituents selected from:

halo, $C_{1-4}$alkyl, $C_{1-4}$alkoxy, $C_{14}$alkylenedioxy, trifluoromethyl, trifluoromethoxy; CN, NO$_2$, amino, mono- and di-alkylamino an Ph(Alk$^1$)$_r$Y(Alk$^2$)$_s$- where Ph is an optionally substituted phenyl; Y is a bond, oxygen or a carbonyl group; Alk$^1$ and Alk$^2$ are independently C$_{1-4}$alkyl which may be straight or branched; and r and s are independently 0 or 1, provided that the length of (Alk$^1$)$_r$Y(Alk$^2$)$_s$ does not exceed 5 atoms, and further provided that:

when X is O and p and q are 0, Ar is not unsubstituted phenyl or phenyl substituted by fluorophenoxy, chloro or methyl; and when X is a bond and the sum of p and q is 1, Ar is not unsubstituted phenyl, or phenyl substituted by amino, methoxy, methyl, dimethylamino, or methylenedioxy;

or a pharmaceutically acceptable salt thereof.

2. A compound according to claim 1 wherein Ar represents phenyl substituted by a group Ph(Alk$^1$)$_r$Y(Alk$^2$)$_s$—.

3. A compound according to claim 2 wherein the sum of r and s is zero or 1.

4. A compound according to claim 3 wherein Alk$^1$ and Alk$^2$ independently represent CH$_2$, C(H)CH$_3$, or C(CH$_3$)$_2$.

5. A compound according to of claim 3 wherein Alk$^1$ and Alk$^2$ independently represent a straight chain C$_{1-4}$alkyl group, provided that the total number of carbon atoms in Alk$^1$ and Alk$^2$ does not exceed 4.

6. A compound according to claim 5 wherein n represents 2.

7. A compound according to claim 6 wherein X represents a bond or oxygen atom.

8. A compound according to claim 7 wherein R$^1$ and R$^2$ independently represent hydrogen or methyl.

9. A compound of formula (I) selected from the group consisting of (±) cis-1-methylamino-2-(4-benzyloxyphenoxy) cyclopentane;

(±) trans-1-methylamino-2-(4-benzyloxyphenoxy) cyclopentane;

(±) cis-1-methylamino-2-(4-benzyloxybenzyl) cyclopentane;

(±) cis-1-amino-2-(4-benzyloxybenzyl)cyclopentane;

(±) cis-1-amino-2-(4-benzoylphenoxymethyl) cyclopentane;

(±) cis-1-amino-2-(4-benzylphenoxymethyl) cyclopentane;

(±) cis-1-methylamino-2-(4-benzylphenoxymethyl) cyclopentane;

(±) cis-1-amino-2-(3,4-dichlorophenoxymethyl) cyclopentane;

(±) cis-1-Amino-2-[4-(4-fluorophenoxy)phenoxymethyl] cyclopentane;

(±) cis-1-Amino-2-[4-(1-methyl-1-phenylethyl) phenoxymethyl]cyclopentane;

(±) cis-1-Methylamino-2-[4-(1-methyl-1-phenylethyl) phenoxymethyl]cyclopentane;

(±) cis-1-Amino-2-[4-(1-(4-fluorophenyl)-1-methylethyl) phenoxymethyl]cyclopentane;

(±) cis-1-Methylamino-2-[4-(1-(4-fluorophenyl)-1-methylethyl)phenoxymethyl]-cyclopentane; or a salt thereof.

10. A process for the preparation of a novel compound of formula (I) which comprises:

(a) when X is O and p and q are both 0, reaction of a compound of formula (II):

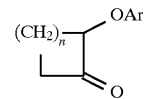

Formula (II)

wherein n and Ar are as hereinbefore defined with a compound R$^1$R$^2$NH wherein R$^1$ and R$^2$ are as hereinbefore defined;

(b) when R$^1$ and R$^2$ are both hydrogen, reduction of a compound of formula (III):

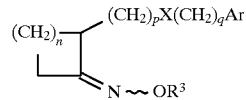

Formula (III)

wherein n, p, q, X and Ar are as hereinbefore defined and R$^3$ is C$_{1-4}$alkyl or phenylC$_{1-4}$alkyl;

(c) when X is O or S reaction of a compound of formula (IV):

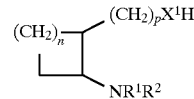

Formula (IV)

wherein R$^1$, R$^2$, p and n are as hereinbefore defined and X$^1$ is O or S, with a compound of formula L(CH$_2$)$_q$Ar wherein L is a leaving group and q and Ar are as hereinbefore defined;

(d) reaction of a compound formula (V):

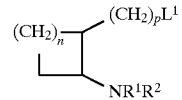

Formula (V)

wherein R$^1$, R$^2$, p and n are as hereinbefore defined and L$^1$ is a group displaceable by a nucleophile, with a compound HX(CH$_2$)$_q$Ar wherein X, q and Ar are as hereinbefore defined;

(e) interconversion of a compound of formula (I) to a different compound of formula (I), and optionally after any of the above processes, forming a salt of formula (I).

11. A pharmaceutical comprising a compound of formula (IB)

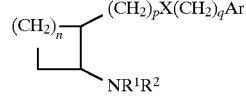

Formula (IB)

wherein

X is O, S, C=O or a bond;

p and q are independently 0–4;

R$^1$ and R$^2$ are each independently selected from the group consisting of hydrogen, C$_{1-6}$alkyl C$_{3-6}$cycloalkyl or C$_{3-6}$cycloalkylC$_{1-4}$alkyl;

n is 1, 2, 3 or 4; and

Ar is phenyl optionally substituted by 1 to 3 substituents selected from:

halo, C$_{1-4}$alkyl, C$_{1-4}$alkoxy, C$_{1-4}$alkylenedioxy, trifluoromethyl, trifluoromethoxy; CN, No$_2$, amino, mono-and di-alkylamino and Ph(Alk$^1$)$_r$Y(Alk$^2$)$_s$- where Ph is an optionally substituted phenyl; Y is a bond, oxygen or a carbonyl group; Alk$^1$ and Alk$^2$ are independently C$_{1-4}$alkyl which may be straight or branched; and r and s are independently 0 or 1, provided that the length of $(Alk^1)_rY(Alk^2)_s$ does not exceed 5 atoms, and further provided that:

when X is O and p and q are 0, Ar is not unsubstituted phenyl or phenyl substituted by fluorophenoxy, chloro or methyl; and when X is a bond and the sum of p and q is 1, Ar is not unsubstituted phenyl, or phenyl substituted by amino, methoxy, methyl, dimethylamino, or methylenedioxy; or a pharmaceutically acceptable salt thereof; and a pharmaceutically acceptable carrier or excipient.

12. A method of treatment of a condition or disease related to the accumulation of calcium in the brain cells of a mammal which comprises administering to a subject in need thereof an effective amount of a compound of formula (I):

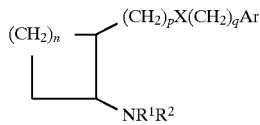

Formula (I)

wherein
X represents O, S, C=O or a bond;
p and q independently represent 0–4;
$R^1$ and $R^2$ each independently represent hydrogen, $C_{1-6}$alkyl, $C_{3-6}$cycloalkyl or $C_{3-6}$cycloalkyl$C_{1-4}$alkyl;
n is 1, 2, 3 or 4; and
Ar represents phenyl optionally substituted by 1 to 3 substituents selected from: halo, $C_{1-4}$alkyl, $C_{1-4}$alkoxy, $C_{1-2}$alkylenedioxy, trifluoromethyl, trifluoromethoxy, CN, $NO_2$, amino, mono- or di- alkylamino and $Ph(Alk^1)_rY(Alk^2)_s$- where Ph is optionally substituted phenyl, Y is a bond, oxygen or a-carbonyl group, $Alk^1$ and $Alk^2$ independently represent $C_{1-4}$alkyl which may be straight or branched and r and s are independently 0 or 1, provided that the length of $(Alk^1)_rY(Alk^2)_s$ does not exceed 5 atoms;
or a pharmaceutically acceptable salt thereof.

13. The method according to claim 12 wherein the disorder is a condition or disease related to an accumulation of calcium in the brain cells of a mammal.

* * * * *